United States Patent [19]

Hignett et al.

[11] 4,200,591

[45] Apr. 29, 1980

[54] CATALYTIC HYDROFORMYLATION

[75] Inventors: Rosemary R. Hignett, Reading; Peter J. Davidson, Woodcote, both of England

[73] Assignee: Johnson, Matthey & Co., Limited, London, England

[21] Appl. No.: 916,534

[22] Filed: Jun. 19, 1978

[30] Foreign Application Priority Data

Jun. 21, 1977 [GB] United Kingdom ............... 25856/77

[51] Int. Cl.² ............................................. C07C 45/10
[52] U.S. Cl. ............................................. 260/604 HF
[58] Field of Search ................................. 260/604 HF

[56] References Cited

U.S. PATENT DOCUMENTS 3,378,590 4/1968 Usami et al. .................. 260/604 HF

FOREIGN PATENT DOCUMENTS 1338225 11/1973 United Kingdom ............. 260/604 HF Primary Examiner—Werren B. Lone
Attorney, Agent, or Firm—Cushman, Darby & Cushman

[57] ABSTRACT

This invention relates to catalytic hydroformylation of internal olefins. In particular the invention relates to a process for the production of a straight chain aldehyde from an olefin comprising reacting said olefin in a liquid reaction medium with hydrogen and carbon monoxide in the presence of a complex of Rh(I) in solution in the said medium as catalyst and a heterogeneous co-catalyst comprising a catalytic metal deposited upon a solid particulate support.

22 Claims, No Drawings

CATALYTIC HYDROFORMYLATION

This invention relates to catalytic hydroformylation reactions; more particularly it relates to the catalytic hydroformylation of internal olefins.

Catalysts frequently used in the hydroformylation of terminal olefins are complexes of Rh(I) with triphenylphosphine. Examples are HRh(CO) (PPh$_3$)$_2$, HRh(CO) (PPh$_3$)$_3$ and (PPh$_3$) Rh(CO) (acac). These catalysts are normally used in solutions in which an excess of triphenylphosphine is present. Using catalysts of this type is now possible to obtain usefully high normal/iso aldehyde ratios when working with terminal olefins. One process by which such catalysts can be used to obtain high normal yields of aldehyde is described in U.S. Pat. No. 4,108,905 or its equivalent British Pat. No. 1,338,225 dated 16th Dec. 1970.

When working with internal olefins however the straight chain product cannot be obtained unless isomerisation in one form or another occurs prior to or during the hydroformylation reaction. It is an object of the present invention to produce normal or straight-chain aldehydes from internal olefins by a process comprising a hydroformylation reaction.

According to one aspect of the present invention a process for the production of a straight chain aldehyde from an olefin comprises reacting the said olefin in a liquid reaction medium with hydrogen and carbon monoxide in the presence of a complex of Rh(I) in solution in the said medium and a heterogeneous co-catalyst comprising a catalytic metal selected from the group consisting of Ru, Rh, Pd, Ir and Pt deposited upon a solid particulate support.

This reaction is most successfully used with short chain internal olefins and is suitable for use with 2-pentene, 2- and 3-hexenes and 2-butene. We prefer to use the olefin itself as the reaction medium. Hydrogen and carbon monoxide are added in gaseous form under pressure but dissolve in the rapidly stirred reaction medium. The solid particulate co-catalyst is suspended in the reaction medium.

The complex of Rh(I) is preferably a complex containing a stabilizing donor ligand.

Preferably the temperature is within the range 115° C.–140° C. and most preferably from 120° C.–130° C.

It has been found to be useful to have a stoichiometric excess of stabilizing donor ligand present in the reaction medium over and above that necessary to form the complex of Rh(I). We have in this invention found it useful to have a ligand:Rh catalyst ratio greater that 1:1 up to about 500:1, where PPh$_3$ is the ligand used a useful ratio is 200:1.

Generally speaking suitable donor ligands for stabilisation purposes are organic compounds having in the molecule a phosphorus atom, such atom being in a valency state such that it possesses a lone pair of electrons. This valency state is normally three. Preferred ligands are often, therefore, tertiary organic phosphines or phosphites:

in which R$^1$, R$^2$ and R$^3$ may be the same or different and may be hydrogen, aryl or alkyl, aralkyl, alkaryl or substituted alkyl, aryl, aralkyl or alkaryl groups.

Conveniently, at least one of the stabilising donor ligands is a phosphorus compound having organic substituents, the phosphorus atom having a valency state possessing a lone pair of electrons. The substituents may be alkyl, aryl, aralkyl, aryloxy, alkoxy, hydroxy, halogeno, amino, amido or nitro groups. Tri-aryl substituted phosphines such as triphenyl phosphine, trinaphthylphosphine and tri-para tolylphosphine are often preferred. The phosphorus compound may be a tri-aryl substituted phosphite, e.g. triphenyl phosphite.

Stabilising donor ligands which may be used in this invention are often described as "biphyllic ligands". By "biphyllic ligand" is meant a compound having an element with a pair of electrons capable of forming a co-ordinate bond with a metal atom and simultaneously having the ability to accept electrons from the metal, thereby providing additional stability to the resulting complex. The term "biphyllic ligand" has been more fully defined by R. G. Pearson in Journal of the American Chemical Society, Volume 82, page 878 (1960).

The stabilising donor ligand which may be used in this invention may be a polydentate compound: This means that it may contain more than one atom which co-ordinates to the central metal atom or ion. In this invention, a stabilising donor ligand or biphyllic ligand might contain more than one phosphorus atom, for example.

The complex hydridocarbonyl tris (triphenyl phosphine) rhodium(I) is stable and can be isolated. We prefer to prepare this complex separately and add it to the reaction medium before commencement of the reaction.

However, we have also found that under the conditions of the reaction, complex rhodium catalysts for use in the process according to the invention may be generated in situ in a number of different ways. For example, if the stabilising donor ligand is a tertiary organo phosphine, complex hydrido carbonyl rhodium complexes suitable for use in the present invention may be generated in situ from compounds such as:

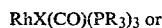

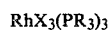

where R is as stated above for R$^1$, R$^2$ and R$^3$ and X is either halogen or pseudo-halogen. With these halogen or halogen-type complexes, an inhibition period is observed before the hydroformylation begins. We have also found that in the presence of acceptors for hydrogen halide, e.g. an organic base such as triethylamine, this inhibition period disappears. A further possibility is therefore the inclusion of a compound such as an organic base which can act as a hydrogen halide acceptor in the reaction medium. Alternatively, the reaction medium itself may act as an acceptor.

Hydrido carbonyl complexes of rhodium which may be used in this invention may also be generated in other ways, e.g. from rhodium compounds in other oxidation states: the rhodium can be added as a simple trivalent salt, e.g. RhCl$_3$, a rhodium carbonyl, e.g. Rh$_6$(CO)$_{16}$, a rhodium II carboxylate Rh$_2$(COOR)$_4$ e.g. rhodium (II) acetate, a rhodium (I) carbonyl carboxylate e.g. ((Rh(CO)$_2$CH$_2$COO))$_2$, a rhodium oxide, rhodium sesquioxide Rh$_2$O$_3$, a rhodium (III) β diketonate such as rhodium acetonylacetonate or a rhodium (I) carbonyl β diketonate, e.g. $Rh(CO)_2 (Acac)$ where Acac is acetyl acetonate.

Particularly useful rhodium complexes which may be used as catalysts in the invention are (Ph=phenyl):

$RhH(CO)(PPh_3)_3$

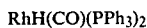
$RhH(CO)(PPh_3)_2$

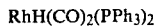
$RhH(CO)_2(PPh_3)_2$

Other useful hydrido carbonyl complexes of rhodium are

$RhH(CO)((P(OPh)_3))_3$

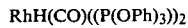
$RhH(CO)((P(OPh)_3))_2$

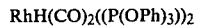
$RhH(CO)_2((P(OPh)_3))_2$

By "catalytic metal" we mean a metal selected from the group comprising Ru, Rh, Pd, Ir, Pt, and alloys thereof in which at least 10% by weight of one or more of the said metals is present. The catalytic metal is preferably deposited upon a particulate support having a particle size within the range 1–500 microns diameter. We prefer powdered carbon although granulated carbon and charcoal may be used. Alternative supports are silica and alumina. We prefer as catalytic metal palladium and alloys thereof. A suitable loading of palladium is 5% by weight on powdered carbon. Approximately equimolar quantities of catalyst and co-catalyst may be used.

EXAMPLE 1

Using a 2-butene substrate we have obtained a normal/iso ratio of 3:1 pentanal using a $H_2:CO=3:1$ and $RhH(CO)(PPh_3)_3$ catalyst at a concentration to give Rh=400 ppm in the reaction medium and 0.3 moles % of 5% Pd/carbon co-catalyst at 130° C.; $pH_2=1.5$ atm; $pCO=0.5$ atm. In the absence of said co-catalyst the normal/iso ratio drops to 1.6. Average particle size of the carbon powder is from 2–5 microns diameter. Analytical technique as in Example 2.

EXAMPLE 2

(a) 0.3 moles of Pd per 100 g. medium in the form of 5% by weight Pd deposited on 50 micron diameter porous carbon powder was used as co-catalyst in a medium consisting of 2- and 3-hexenes (60:40 by weight) as substrate/solvent. The catalyst was 400 ppm Rh(I) present as $RhH(CO)(PPh_3)_2$ or $_3$ and 20% by weight of substrate excess $PPh_3$ was present. The molar ligand:catalyst was therefore approximately 175. At 130° C. and 1.5 atm. $H_2$ and 0.5 atm. CO a n/iso heptaldehyde ratio of 3.0:1 was obtained. This should be compared with 1.6:1 n/iso ratio without co-catalyst.

(b) Two repetitions of this experiment gave n/iso ratios of 2.7:1 and 2.0:1. The normal/iso isomer ratio of $C_7$ aldehyde (heptanal) was measured by vapour phase chromatography using a 5 ft column having an OD of 0.25 inches packed with 10% SE 30 on Chromosorb W and operated at 75° C.

EXAMPLE 3

$Pd(acac)_2$ deposited at 5% by weight Pd upon 100 micron diameter porous $SiO_2$ was used as co-catalyst in suspension at a concentration of 8.2 g/l. Using a molar ratio of Pd:Rh of 1:1, 400 ppm Rh present as $RhH(CO)(PPh_3)_3$ and 20% by weight $PPh_3$ in 2- and 3-hexene (60:40 by weight) substrate/solvent we obtained an n/iso ratio of 2.2:1 at 130° C. and 1.5 atm. $H_2:0.5atm.CO$. The same analytical technique was used as in Example 2.

EXAMPLE 4

In this case Rh was used both as catalyst and as co-catalyst. Using 5% by weight Rh deposited on 100 micron diameter porous $Al_2O_3$ at 1:1 molar with 400 ppm Rh present as $RhH(CO)(PPh_3)_3$ in 2- and 3-hexenes (60:40 by weight) substrate/solvent with 20% by weight of $PPh_3$ added. n/iso ratio 2.2:1. The same analytical technique was used.

What we claim is:

1. A process for the production of a straight chain aldehyde from an internal olefin selected from the group consisting of 2-pentene, 2-hexene, 3-hexene and 2-butene which comprises reacting said olefin at a temperature of 115° to 140° C. in a liquid reaction medium and at an elevated pressure less than 200 psi with hydrogen and carbon monoxide in the presence of an hydride carbonyl complex of Rh(I) including a triaryl phosphine or triaryl phosphite stabilizing donor ligand, said complex being in solution in the said medium as catalyst and a heterogeneous co-catalyst comprising a catalytic metal deposited upon a solid particulate support, said catalytic metal being a metal selected from the group consisting of Ru, Rh, Pd, Ir, Pt and alloys thereof in which at least 10% by weight of one or more of the said metals is present, the molar ratio in the reaction medium of catalytic metal deposited upon the catalyst support to catalyst being within the range 20:1 to 1:20.

2. A process according to claim 1 in which an approximately equimolar ratio of catalytic metal in the co-catalyst and catalyst is used.

3. A process according to claim 1 in which the triaryl phosphite is triphenyl phosphite.

4. A process according to claim 1 wherein the triaryl phosphine is triphenyl phosphine.

5. A process according to claim 1 in which the hydrido carbonyl complex of rhodium is

$RhH(CO)(PPh_3)_3$ or

$RhH(CO)(PPh_3)_2.$

6. A process according to claim 1 in which the hydrido carbonyl complex of rhodium is

$RhH(CO)((P(OPh)_3))_3$ or

$RhH(CO)((P(OPh)_3))_2.$

7. A process according to claim 1 in which the hydrido carbonyl complex of rhodium is

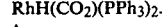
$RhH(CO_2)(PPh_3)_2.$

8. A process according to claim 1 in which the hydrido carbonyl complex of rhodium $RhH(CO)_2((P(OPh)_3))_2.$ 9. A process according to claim 1 wherein the hydrido carbonyl complex is generated in situ.

10. A process according to claim 9 wherein the hydrido carbonyl complex is generated from $$RhX(CO)(PR_3)_3$$

or $$RhX_3(PR_3)_3$$

or $$RhX(CO)(PR_3)_2$$

where X is a halogen or pseudo-halogen and R is an alkyl, aryl, aralkyl, alkaryl, or substituted alkyl, aryl, aralkyl or alkaryl group.

11. A process according to claim 10 including an acceptor for hydrogen halide.

12. A process according to claim 11 wherein the acceptor is an organic base.

13. A process according to claim 12 wherein the organic base is triethylamine.

14. A process according to claim 13 wherein the acceptor is the phosphorus-containing stabilizing donor ligand.

15. A process according to claim 9 in which the source of rhodium is a trivalent rhodium salt, a rhodium carbonyl, a rhodium (II) carboxylate, a rhodium (I) carbonyl carboxylate, a rhodium oxide, a rhodium (III) β-diketonate, or a rhodium carbonyl β-diketonate.

16. A process according to claim 15 wherein the rhodium carboxylate is the acetate.

17. A process according to claim 15 wherein the β-diketonate is acetylacetonate.

18. A process according to any preceding claim wherein the molecular ratio of $H_2:CO$ is within the range 1:15 to 5:1.

19. A process according to claim 18 wherein the molecular ratio of $H_2:CO$ is within the range 5:1 to 1:6.

20. A process according to claim 1 wherein the temperature range is 120° C.–130° C.

21. A process according to claim 1 wherein the ligand/catalyst ratio lies within the range of 1:1 to 500:1.

22. A process according to claim 2 wherein the ligand/catalyst ratio is 200:1.

* * * * *